US006506055B1

(12) United States Patent
Pashley et al.

(10) Patent No.: US 6,506,055 B1
(45) Date of Patent: Jan. 14, 2003

(54) METHOD OF REDUCING DENTIN SENSITIVITY AND COMPOSITIONS THEREFOR

(75) Inventors: David H. Pashley, Augusta, GA (US); Ricardo M. Carvalho; Jose C. Pereira, both of Sao Paulo (BR)

(73) Assignee: MCG Research Institute, Augusta, GA (US)

( * ) Notice: Subject to any disclaimer, the term of this patent is extended or adjusted under 35 U.S.C. 154(b) by 0 days.

(21) Appl. No.: 09/417,868

(22) Filed: Oct. 13, 1999

(51) Int. Cl.$^7$ .............................. A61K 6/08; A01N 1/02; A61C 13/23; C08K 5/07; C08L 31/00
(52) U.S. Cl. ..................... 433/228.1; 106/35; 424/49; 424/55; 522/79; 522/84; 523/116; 523/118
(58) Field of Search .................... 424/49–58; 523/116, 523/118; 106/35; 433/228.1

(56) References Cited

U.S. PATENT DOCUMENTS

| | | | | |
|---|---|---|---|---|
| 4,057,621 A | * | 11/1977 | Pashley et al. | 424/49 |
| 4,514,527 A | * | 4/1985 | Bowen | 523/115 |
| 4,521,550 A | * | 6/1985 | Bowen | 523/116 |
| 4,538,990 A | * | 9/1985 | Pashley | 433/217 |
| 4,588,756 A | * | 5/1986 | Bowen | 523/116 |
| 4,659,751 A | * | 4/1987 | Bowen | 523/116 |
| 4,964,911 A | * | 10/1990 | Ibsen et al. | 106/35 |
| 5,098,297 A | | 3/1992 | Chari et al. | |
| 5,256,065 A | | 10/1993 | Nicholson | |
| RE34,937 E | * | 5/1995 | Ibsen et al. | 106/35 |
| 5,700,148 A | | 12/1997 | Fischer et al. | |
| 5,722,833 A | | 3/1998 | Fischer et al. | |
| 5,766,012 A | | 6/1998 | Rosenbaum et al. | |
| 5,844,019 A | * | 12/1998 | Kato | 523/116 |
| 5,847,020 A | * | 12/1998 | Ibsen et al. | 522/84 |
| 5,874,066 A | * | 2/1999 | Hack et al. | 424/49 |
| 5,906,809 A | * | 5/1999 | Hack et al. | 424/49 |
| 5,922,786 A | * | 7/1999 | Mitra et al. | 523/119 |
| 6,004,390 A | * | 12/1999 | Pflug et al. | 106/35 |
| 6,031,016 A | * | 2/2000 | Ibsen et al. | 522/79 |

OTHER PUBLICATIONS

Eick, et al, Current Concepts on Adhesion to Dentin, *Crit Rev Oral Biol Med* 8(3):306–335 (1997).
Pashley, Dentine Permeability and Its Role in the Pathobiology of Dentine Sensitivity, *Archs oral Biol.* vol. 39, Suppl., pp. 73s–80s (1994).
Brannstrom, Communication, Between the Oral Cavity and the Dental Pulp Associated with Restorative Treatment, *Operative Dentistry*, 9, 57–68 (1984).
Brannstrom, et al, The Hydrodynamics of the Dentine; Its Possible Relationship to Dentinal Pain, *Reprint from The International Dental Journal* vol. 22 No. 2, (Jun. 1972).

Pashley, Dentin Permeability, Dentin Sensitivity, and Treatment Through Tubule Occlusion, *Journal of Endodontics*, vol. 12, No. 10, (Oct. 1986).
Greenhill, et al, The Effects of Desensitizing Agents on the Hydraulic Conductance of Human Dentin in vitro *J Dent Res* 60(3):686–698 (March 1981).
Kontturi–Narhi, Dentin Hypersensitivity—Factors Related to the Occurrence of Pain Symptoms, *Kuopio University Publications D. Dental Sciences* 5, (1993).
Kerns, et al, Dentinal Tubule Occlusion and Root Hypersensitivity, *J Periodontol* 62:421–428, (Jul. 1991).
Yoshiyama, et al, Morphological characterization of hypersensitive human radicular dentin and the effect of a light–curing resin liner on tubular occlusion, *Proc Finn Dent Soc*, 88 Suppl 1, 337–44, (1992).
Tavares, et al Using a Flouride–Releasing Resin to Reduce Cervical Sensitivity, *JADA*, vol. 125, pp. 1337–1342 (Oct. 1994).
Tay, et al A Scanning Electron Microscopic Study of the Extent of Resin Penetration into Human Coronal Dentin Following a Total Etch Technique In Vivo, *Cells and Materials*, vol. 4, No. 4, pp. 317–329 (1994).
Craig, *Restorative Dental Materials,* Ninth Edition, Mosby p. 43.
Pashley, et al Effects of oxalate on dentin bonding, *American Journal of Dentistry*, vol. 6, No. 3, pp. 116–118, (Jun. 1993).
Chan, et al, A short– and long–term shear bond strength study using acids of varying dilutions on bovine dentine, *Journal of Dentistry*, vol. 25, No. 2, pp. 145–152 (1997).
Gerzina, et al, Effect of Hydrostatic Pressure on the Diffusion of Monomers through Dentin in vitro, *J Dent Res* 74(1): 369–373, (Jan. 1995).
Bouillaguet, et al In Vitro Cytotoxicity and Dentin Permeability of HEMA, *Journal of Endodontics*, vol. 22, No. 5, pp. 244–248, (May 1996).
Meerbeek, et al Clinical Status of Ten Dentin Adhesive Systems, *J Dent Res* 73(11): 1690–1702, (Nov. 1994).
Pashley, et al, The Effects of Oxalate Treatment on the Smear Layer of Ground Surfaces of Human Dentine, *Archs oral Biol.*, vol. 30, No. 10, pp. 731–737 (1985).

* cited by examiner

Primary Examiner—Shep K. Rose
(74) Attorney, Agent, or Firm—Clark G. Sullivan, Esq.; King & Spalding

(57) ABSTRACT

A method of reducing dentin sensitivity comprising: applying an effective amount of an acid to a dentin surface to form a treated surface; and administering an effective amount of an acidic oxalate to the treated surface so as to occlude dentinal tubules beneath the dentin surface. The method may optionally comprise the subsequent application of a suitable bonding agent. The invention further provides a kit for the treatment of dentin sensitivity, comprising a first container of an acid treatment composition, and a second container of an acidic oxalate composition.

10 Claims, 9 Drawing Sheets

METHOD OF REDUCING DENTIN SENSITIVITY AND COMPOSITIONS THEREFOR

ACKNOWLEDGMENTS

This invention was made with government support under USPHS Grant DE06427 awarded by the National Institute of Dental Research. The government has certain rights in the invention.

BACKGROUND OF THE INVENTION

Field of the Invention

This invention relates generally to methods for reducing dental sensitivity resulting from exposed dentin that has lost its natural coverings of enamel or cementum.

Many patients complain of tooth sensitivity to hot and cold drinks and to certain acidic or hypertonic foods. This sensitivity often occurs when gum tissue recedes from the necks of teeth, exposing root surfaces that are not covered by hard enamel but by soft cementum. The cementum is so thin and soft that it can be removed by tooth brushing, thereby exposing the sensitive underlying dentin. The dentin can also become exposed under restorations. The pain that patients feel from exposed dentin is called dentin sensitivity, as reported in Pashley, Arch Oral Biol 39 (Suppl) 735–805 (1994).

Dentin sensitivity, whether on exposed surfaces at the necks of teeth or under restorations, is reportedly due to minute fluid shifts across dentin in response to painful stimuli (Brännström, Oper Dent 9: 59–68, 1984). This theory, called the hydrodynamic theory, (Brännström and Aström, Int Dent J 22: 219–j226, 1972), assumes that fluid can move within or through the microscopic tubules making up dentin, at a rate that activates mechanoreceptor nerves in the dentin pulp. A corollary to this theory is that anything that decreases the ease with which fluid can move across dentin should decrease dentin sensitivity (Pashley, J Endodont 12: 465–476, 1986). A number of agents have been previously screened for their ability to occlude dentinal tubules, including potassium oxalate (Greenhill and Pashley, J Dent Res 60: 686–698, 1981). When 3% w/v acidic monopotassium-monohydrogen oxalate is applied to dentin, the hydraulic conductance of dentin is reduced both in vitro and in vivo (Pashley, J Endodont 12: 465–476, 1986). It has been reported that the soluble oxalate reacts with ionized calcium in dentinal fluid or on dentin to form insoluble crystals of calcium oxalate. U.S. Pat. No. 4,057,621. Compositions and uses of solutions and gels that contain concentrations of neutral and acidic monopotassium-monohydrogen oxalates are outlined in U.S. Pat. Nos. 4,057,621 and 4,538,990. Although such treatments have been shown to decrease dentin sensitivity clinically (Konttari-Närhi, Ph.D. thesis, University of Kuopio, Kuopio, Finland, 1993), the crystals have a finite solubility, and can solubilize from the dentin surface within one week (Kerns et al., J Periodont 62: 421–428, 1991). Moreover, because the crystals are on the surface, patients can remove them by daily brushing, and thereby cause a recurrence of dentin sensitivity.

Adhesive resin monomers have also been advocated for treating dentin sensitivity. (Yoshiyama, Proc Finn Dent Soc 88 (Suppl 1) 337–344, 1992; Tavares, J Am Dent Assoc 125: 1337–1342, 1994). Such adhesives protect the dentin by forming a thin layer (ca. 20–50 $\mu$m thick) on the surface of the dentin. Because of their limited strength, and their thinness, adhesive resins can generally be easily removed from the dentin surface by daily brushing.

Recent improvements in resin adhesives include the development of monomers that are much more hydrophilic, unlike previous versions that were hydrophobic. This property permits resin monomers to penetrate water-filled tubules where they can form resin-droplets or micelles or even solid resin tags that penetrate into the tubules and bond to the walls of the tubules (Tay et al., Cells and Mater 4: 317–329, 1994). Under these conditions, it is the resin tags that actually occlude the tubules. However, many polymers obtained from these monomers have a coefficient of thermal expansion that is much higher (71–94×10$^{-6}$/° C.) than that of dentin (11.4×10$^{-6}$/° C., Craig, Restorative Dental Materials, 9th ed., Mosby, St. Louis, p. 43, 1993). Cold foods and liquids may cause the resin tags to shrink, allowing movement of dentinal fluid around them at a rate that may cause pain. Moreover, the resin often shrinks during polymerization, producing only partial tubule occlusion.

Thus, neither oxalates nor resins have proven completely effective to reduce dentin sensitivity for a prolonged period of time. Moreover, it has also been reported that the combination of oxalate and resin is not effective to reduce dentin sensitivity for a prolonged period of time, because the adhesive resins do not bond well to oxalate-treated dentin. (Pashley, Tao and Pashley, Am J Dent 6: 116–118, 1993). This is due to the physical presence of crystals of calcium oxalate on the dentin surface that prevents an intimate attachment of the resin to the underlying dentin surface. What is needed, therefore, is a method of reducing dentin sensitivity for a prolonged period of time, and that withstands the abrasive effects of regular brushing.

SUMMARY OF THE INVENTION

The above disadvantages of the prior art are overcome by the present invention which relates to a method of reducing dentin sensitivity for extended periods of time by acid pre-treating the dentin surface before applying an acidic oxalate to the dentin surface. The resulting dentin is substantially less subject to dentin sensitivity, and the treatment endures for a prolonged period of time. The resulting dentin is also substantially more receptive to bonding agents which can be applied over the oxalate-treated dentin to obtain an even more durable and prolonged treatment.

Thus, in accordance with the purpose(s) of this invention, as embodied and broadly described herein, this invention in one aspect relates to a method of reducing dentin sensitivity comprising: applying an effective amount of an acid to a dentin surface to form a treated surface; and administering an effective amount of an acidic oxalate to the treated surface so as to occlude dentinal tubules beneath the dentin surface. The method may optionally comprise the subsequent application of a suitable bonding agent.

Another aspect of the invention provides a kit for the treatment of dentin sensitivity, comprising a first container of an acid treatment composition, and a second container of an acidic oxalate composition. The kit may also comprise a suitable bonding agent.

Additional aspects and advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE PREFERRED EMBODIMENTS

Figure 1A:
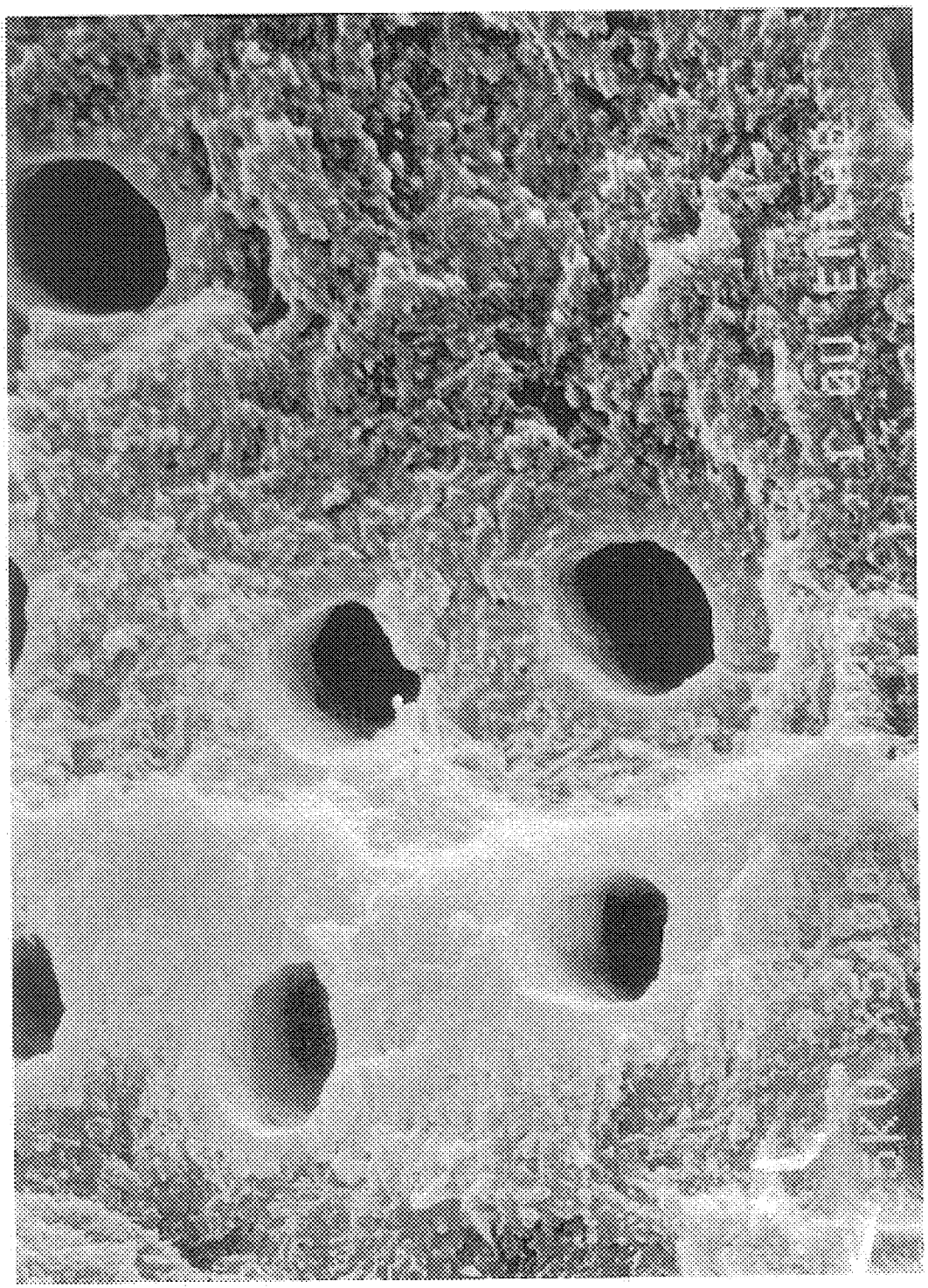
FIG. 1A is a scanning electron micrograph ("sometimes called an SEM") of a mineralized dentin surface with open orifices that are similar to those found in hypersensitive dentin.
Figure 1B:
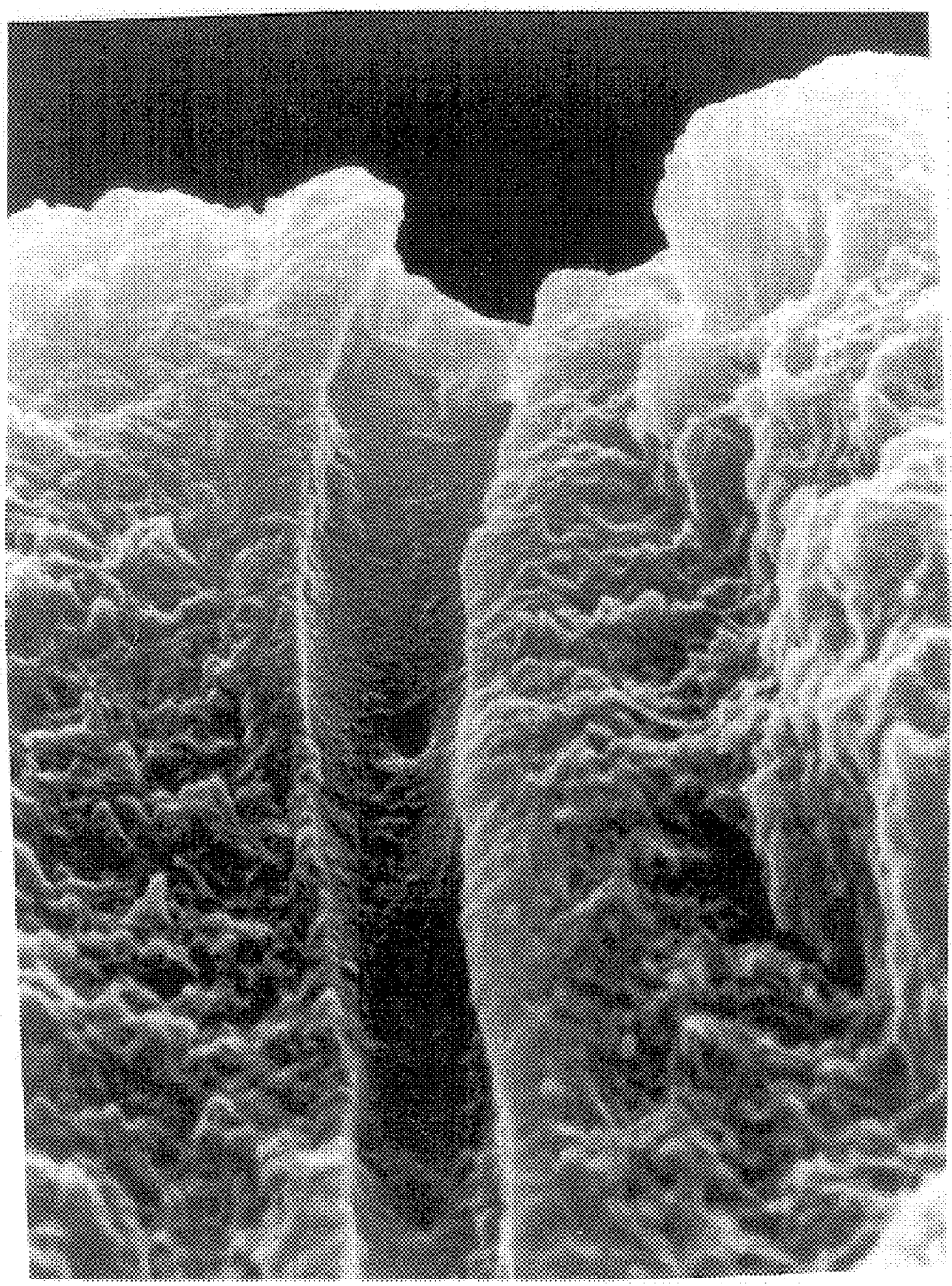
FIG. 1B is a scanning electron micrograph of the fractured edge of the specimen in FIG. 1A. Note that the tubules are empty.

The present invention may be understood more readily by reference to the following detailed description of preferred embodiments of the invention and the Examples included therein. Before the present compounds, compositions and methods are disclosed and described, however, it is to be understood that this invention is not limited to specific methods, specific compositions, or to particular pharmaceutical formulations or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a bonding agent" includes mixtures of bonding agents, reference to "a pharmaceutical carrier" includes mixtures of two or more such carriers, and the like.

Ranges are often expressed herein as from about one particular value, and/or to about another particular value. When such a range is expressed, it is to be understood that a more preferred range is typically from the one particular value and/or to the other particular value. Similarly, when values are expressed as approximations, by use of the antecedent "about," it will be understood that the particular value is typically more preferred.

In this specification and in the claims that follow, reference will be made to a number of terms which shall be defined to have the following meanings:

A residue of a chemical species, as used in the specification and concluding claims, refers to the moiety that is the resultant product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, the residue of a solubilized salt refers to the anion and cation of the salt in solution, regardless of whether the anion and cation were obtained by dissolving the salt in solution.

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

By "pharmaceutically acceptable" is meant a material that is not biologically or otherwise undesirable, i.e., the material may be administered to an individual along with the selected pharmaceutical composition without causing any undesirable biological effects or interacting in a deleterious manner with any of the other components of the pharmaceutical composition in which it is contained.

Acid etchant means any acidic composition that contains an acidic ingredient, and which is suitable for solubilizing calcium phosphate from the surface and subsurface of teeth in vitro.

The term "acidic oxalate" refers to any composition that contains a residue of oxalic acid, or an oxalic acid derivative, that is capable of penetrating dentin tubules and reacting with the calcium phosphate below the dentin surface, to form calcium oxalate crystals in the tubules below the dentin surface. Thus, the acidic oxalate may be obtained by solubilizing oxalic acid, or by solubilizing any salt obtained from oxalic acid, in a suitable pharmaceutically acceptable carrier.

The present invention provides a method of decreasing the sensitivity of dentin, using oxalates, in a manner that does not interfere with subsequent resin bonding. The method is performed by applying an effective amount of an acid to a dentin surface to form a treated surface, and administering an effective amount of an acidic oxalate to the treated surface so as to occlude dentinal tubules beneath the dentin surface. The acid etchant is applied in a manner that depletes an effective amount of calcium phosphate from the dentin surface, to an effective depth below the dentin surface. The acid etchant preferably depletes the surface and immediate subsurface of dentin of most or all of its calcium phosphate. By immediate subsurface is meant that depth beneath the surface of dentin which, when treated to remove calcium phosphate, is receptive to the subsequent treatment disclosed herein. In a particular embodiment, the acid etchant preferably depletes 1–15 $\mu$m of dentin of most or all of its calcium phosphate, and even more preferably depletes the top 3–7 $\mu$m of dentin of most or all of its calcium phosphate.

The acid treatment can be carried out with any acid etchant that is capable of removing an effective amount of calcium phosphate to an effective depth beneath the dentin surface, and that does not detrimentally affect the dentin or other dental structures with which the acid comes into contact, such as tooth enamel or gums. Suitable acid etchants and acid treatment processes are generally known to workers skilled in the art and include, for example, the etchants and acid treatment processes described in Chan et al., J. Dent. 25:145–152 (1997), the disclosure from which being hereby incorporated by reference.

The acid etchant preferably has a pH of from about –0.2 to about 3.5, and more preferably from about 0.5 to about 2.0. The acidic ingredient comprising the acid etchant preferably has a pKa of less than three, and more preferably of from about 1 to about 3. The concentration of the acidic ingredient can also vary, but generally ranges from about 0.1% by weight to saturation, and preferably ranges from about 10 to about 38% by weight. Similarly, the time required for the acid treatment varies with the pH and concentration of the acid etchant, but generally ranges from 5–60 seconds.

The acid etchant is typically present as a gel, because of the ease with which the gel can be handled and applied. Liquids, suspensions, lotions, creams, and the like may also be used, as long as the acidic ingredient can be delivered to the surface of the dentin. Both mineral and organic acids can be employed. A 10% (by weight) phosphoric acid gel (All-Etch) available from Bisco Dental Products in Itasca, Ill., is especially suitable, although commercially available 37% (by weight) phosphoric acid gels are also especially appropriate. The acid treatment generates a residue containing solubilized calcium phosphate, that is preferably removed before further treatment of the dentin surface. Any residue from the acid treatment is preferably rinsed from the dentin surface with a pharmaceutically acceptable liquid such as water.

The acid treatment is followed by treating the dentin surface with an acidic oxalate, typically in the form of a solution or gel. Liquids, suspension, lotions, creams and the like may also be used, as long as the active oxalic component of the acidic oxalate can be delivered to the surface of the dentin. The acidic oxalate preferably has an acidic pH ranging from about 1 to about 6, and even more preferably the pH of the acidic oxalate ranges from about 2 to about 5.

The acidic oxalate can be obtained by solubilizing oxalic acid or any salt of oxalic acid in a pharmaceutically acceptable carrier. Any soluble salt is appropriate, including salts comprising aluminum, zinc, copper, nickel, cobalt, strontium, stannous, iron and magnesium elements. All of the alkali metal salts of oxalic acid, as well as the ammonium salts and dihydrogen oxalate are especially effective. Monobasic salts of oxalic acid, i.e. salts of oxalic acid in which only one of the two oxalate moieties of the oxalic acid is reduced by a suitable base, are preferably employed.

The acidic oxalate may contain the oxalic acid salt, or dihydrogen oxalate, generally at a concentration ranging from about 0.5% (w/v of solution, measured as grams of composition dissolved in 100 ml. of solution), up to the saturation point for the oxalic compound. The acidic oxalate preferably comprises from about 0.5 to about 3% (w/v of solution) of a monobasic salt of oxalic acid. The acidic oxalate may further comprise a suitable thickening agent if a gel if desired.

In a particularly preferred embodiment the acidic oxalate is obtained by solubilizing about 60 grams of dipotassium oxalate in about 1 L of distilled water. About 30 grams of hydroxyethyl cellulose are added to increase the viscosity of the solution, and to obtain a gel. The resulting gel is preferably titrated to a pH of 4.0. Particularly suitable compositions of solutions and gels that contain acidic monopotassium-monohydrogen oxalate are outlined in U.S. Pat. Nos. 4,057,621 and 4,538,990, the disclosure from which are hereby incorporated by reference.

When the acidic oxalate is applied to the surface of acid-etched dentin it penetrates the surface and immediate subsurface of the dentin, which is substantially free of surface calcium phosphate (due to the prior acid treatment) that would otherwise interfere with the penetration of the acidic oxalate. The acidic oxalate travels through the dentin tubules substantially unhindered until it encounters and reacts with mineralized dentin, i.e. dentin that contains calcium phosphate, often at about 3–15 $\mu$m beneath the dentin surface. At this subsurface site, the acidic oxalate dissolves calcium and forms subsurface calcium oxalate crystals. As the acidic oxalate penetrates even further beneath the dentin surface, larger crystals of calcium oxalate are formed as the acidic oxalate encounters more and more calcium. This crystal growth in many cases can almost completely occlude the tubule lumina beginning 5–8 $\mu$m below the dentin surface, and extending to about 15–20 $\mu$m below the dentin surface.

The dentin thus obtained is substantially impervious to fluid shifts across the calcium oxalate filled tubules. Because the calcium oxalate is slightly soluble, however, the dentin does not remain impervious indefinitely. To prolong the impervious feature of the dentin, the dentin may optionally be treated with a suitable bonding agent for sealing the surface of the dentin. Suitable bonding agents are also capable of penetrating the space in the open tubule lumen above the calcium oxalate crystals, and hardening to yield a hydrophobic barrier (or "tag") that further protects the calcium oxalate crystals from the solubilizing effects of oral fluids.

Many suitable bonding agents are known in the field of dentistry, and include both organic solvent and aqueous based agents. Suitable bonding agents include adhesive primers, resins, adhesive cements, nonadhesive cements, direct dental restorations, and indirect dental restorations. These bonding agents are preferably hydrophilic before they harden, which enables them to penetrate the aqueous filled dentinal tubules before hardening. The generic composition of hydrophilic primers is usually an aqueous or acetone solution of 2-hydroxymethacrylate, or polyalkenoic acid, or dipentaerythiritol pentaacrylate phosphoric acid ester. A general discussion of suitable hydrophilic primers is contained in Eick et al., Critical Rev. in Oral Biol. Med. 8: 306–335 (1997) (the disclosure from which being hereby incorporated by reference). Particularly suitable bonding agents include the acetone based agent manufactured by Bisco, in Itasca, Ill., under the trade name "One Step," and the aqueous based agent sold by 3M Dental Products in St. Paul, Minn., under the trade name Scotchbond Multi-Purpose Plus bonding adhesive. Other exemplery bonding agents include All Bond from Bisco, Single Bond from 3M, and Optibond and Optibond Solo from Kerr. After application of the bonding agent, other materials can be applied to the dentin surface, such as composite resin buildups, in order to complete the restoration of a cavity preparation or toughen the surface of the resin if it was applied to an exposed tooth surface.

From this combined treatment there is obtained an effective seal that prolongs the desensitizing effect of oxalates over what would have occurred in the absence of the use of a bonding agent. Even if some of the bonding agent is lost from the surface of the dentin, the residual resin tags within the tubules continue to give an excellent synergistic desensitizing effect. The presence of calcium oxalate crystals within dentinal tubules also prevents bonding agents from penetrating too deeply into open tubules, thereby protecting the dentinal pulp from the potential irritating properties of resin monomers, as reported in Gerzina and Hume, J. Dent. Res. 74:369–373, 1995, and Bouillaguet et al., J. Endont 22:244–248, 1996. Moreover, because the oxalate crystals are formed below the surface, the dentin surface remains available for bonding with suitable agents. This permits the development of high bond strengths, that correlate well with the excellent clinical retention results for bonded composite resin restorations reported in Van Meerbeek et al., J. Dent. Res. 73: 1690–1702 (1994).

The compounds of the invention may be readily synthesized using techniques generally known to synthetic organic chemists. Suitable experimental methods for making and deriving the compounds are described, for example, in the references cited in the Background section herein above, the disclosures of which are hereby incorporated by reference for their general teachings and for their synthesis teachings. Methods for making specific and preferred compounds of the present invention are described in detail in the Examples below.

EXPERIMENTAL

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, depths, etc.) but some errors and deviations should be accounted for. Unless indicated otherwise, parts are parts by weight, temperature is in ° C. or is at room temperature, and pressure is at or near atmospheric.

The acidic oxalate used in these examples was prepared by adding 60 grams of dipotassium oxalate (DKO) to 1 L of distilled water. After dissolving the oxalic acid, 30 grams of hydroxyethyl cellulose were added to increase the viscosity of the solution to a 6% DKO gel that was titrated to give a pH of 4.0. The 10% phosphoric acid. gel was obtained from Bisco in Itasca, Ill.

Example 1

Acidic Oxalate Results

Twelve human extracted third molars were prepared by making two parallel sections using a diamond abrasive saw blade at right angles to the long axis of the root. The first section removed all of the occlusal enamel and exposed middle coronal dentin. The second section removed the roots 2 mm below the cementoenamel junction, in a manner described by Pashley et al. in Am J Dent 6: 116–118 (1993), yielding a crown segment contaning the top of the coronal pulp chamber covered by dentin, and a smear layer over the dentin. The crown segment was then glued to a piece of Plexiglas that was penetrated by an 18 gauge needle that was used to fill the pulp chamber with a physiological salt solution. The mounted crown segment was then attached to an apparatus used to measure the permeability of the exposed dentin, i.e. fluid flow across the dentin, as described in Pashley et al., Arch Oral Brol 30: 731–737 (1985). The ease with which fluid could flow across the dentin was measured before and after acid etching in the twelve teeth.

After measuring control fluid flow across the smear layer-covered dentin surfaces of the mounted crown segments, the dentin surfaces were etched with 10% phosphoric acid gel for 20 seconds followed by rinsing with water. The permeability of the dentin was then remeasured. The acid-etched surfaces were next treated topically with the 6% DKO gel for 60 seconds followed by rinsing with water, and the permeability again measured. The results of the permeability studies are shown in Table 1.

TABLE 1

Dentin permeability results

| Treatment | Dentin permeability (% of maximum) |
| --- | --- |
| No Treatment (smear layer-covered) | $10.7 \pm 3.4(12)^a$ |
| Acid etched (10% $H_3PO_4$) | 100.0 (12) |
| Acid etched followed by DKO gel treatment (60 seconds) | $12.1 \pm 2.1(12)^a$ |

Identical lower case letters designate groups that are not statistically different ($p > 0.05$).
Numbers in parentheses indicate the number of teeth in each group.

Measurement of the permeability of smear layer-covered dentin indicated that it has a low permeability ($10.7 \pm 3.4\%$) compared to acid etched values that were assigned a value of 100%.

Acid-etching the dentin removed the smear layer debris occluding the dentinal tubules created during specimen preparation and increased dentin permeability to its maximum value, thereby simulating the clinical condition of dentin sensitivity, as reported in Pashley, J Endodont 12: 465–474 (1986). Subsequent treatment of the acid-etched experimental group with the (6% DKO) gel reduced the permeability of the dentin down to values that were not statistically different from smear layer values.

Example 2

Bond Testing Results

To test the effects of oxalate treatment of pre-acid etched dentin on resin-dentin bond strengths, twenty teeth were prepared for bonding by grinding off their occlusal enamel to expose flat dentin surfaces. All of the teeth were acid-etched with 10% phosphoric acid for 20 seconds and then rinsed with water for 15 seconds. Ten of the teeth were assigned to a control group and were treated with 0.9% NaCl for 60 seconds, and then rinsed with water for 15 seconds. The other ten of the teeth, the experimental group, were treated with the 6% DKO gel for 60 seconds and then rinsed with water for 15 seconds. Five teeth in each group were bonded with One Step (Bisco, Itasca, Ill.) while the other five teeth from each group were bonded with Scotchbond Multi-Purpose Plus (3M Dental Products, St. Paul, Minn.). After bonding the dentin surfaces, all teeth received composite resin (Z100, 3M) buildups. They were then soaked in water at 37° C. for 24 hours, followed by preparation for micro tensile testing according to the method reported in Sano et al., Dent. Mater. 10: 236–240 (1994). Each tooth yielded 4 useable specimens, for a total of 20 specimens per group. The results are shown in Table 2.

The average (±S.D.) bond strengths of the One-Step system in the control group was 25.9±9.2 MPa while the average bond strength in the experimental group was 27.9±8.9 MPa (N=20), a value that is not statistically different (p>0.5). When another bonding system (Scotchbond Multi-Purpose Plus) was used that utilizes an aqueous based primer, the results were similar (Table 2). The tensile bond strengths of control group specimens bonded with Scotchbond Multi-Purpose Plus bonding adhesive (3M Dental Products, St. Paul, Minn.) was 23.0±1.9 MPa (N=20), while the experimental group specimens bonded with the same bonding system was 22.9±9.6 MPa (p=0.99).

This result demonstrated that oxalate treatment of previously acid etched dentin does not lower resin bond strength, unlike oxalate treatment of unetched dentin (Pashley, Am J Dent 6: 116–118, 1993) in which bond strengths made to oxalate treated unetched dentin ranged between 1–5 MPa.

TABLE 2

Effects of oxalate treatment of preacid etched dentin on tensile bond strengths.

| Bonding Agent | Tensile Bond Strength (MPa) | | |
|---|---|---|---|
| | NaCl Control | p value | Oxalate Treatment |
| One-Step | 25.9 ± 9.2(20) | 0.50 NS | 27.9 ± 8.9(20) |
| Scotchbond Multi-Purpose Plus | 23.0 ± 7.9(20) | 0.99 NS | 22.9 ± 9.6(20) |

NS = not statistically significantly different. Numbers in parenthesis are the number of specimens in the samples.

The dentinal tubules of additional specimens that were not subjected to tensile bond tests were examined by high-resolution scanning electron microscopy (SEM) to determine the presence and distribution of calcium oxalate crystals within the tubules. Four groups of specimens were prepared as described above. In Group 1, the dentin surfaces were ground to prepare mineralized dentin surfaces with open dentinal tubules. Some of these mineralized specimens were treated with 6% DKO gel for 1 min to produce surface occlusion of dentinal tubules. All other groups (2–4) were acid-etched with 10% phosphoric acid gel for 20 seconds followed by rinsing with water. Group 2 acid-etched control specimens were topically treated with 3% NaCl for 1 min, and rinsed. Group 3 specimens were acid-etched and then treated with 6% DKO gel for 1 min and then rinsed with water. Group 4 specimens were treated in the same manner as Group 3 specimens, but were then treated with the One-Step (Bisco, Itasca, Ill.) adhesive bonding system. All specimens were then frozen in liquid nitrogen and fractured to permit examination of the contents of the dentinal tubules beneath the surface. They were then air-dried overnight in a vacuum, coated with a thin layer of gold and examined in a SEM. The results are shown in FIGS. 1–5.

Figure 2A:
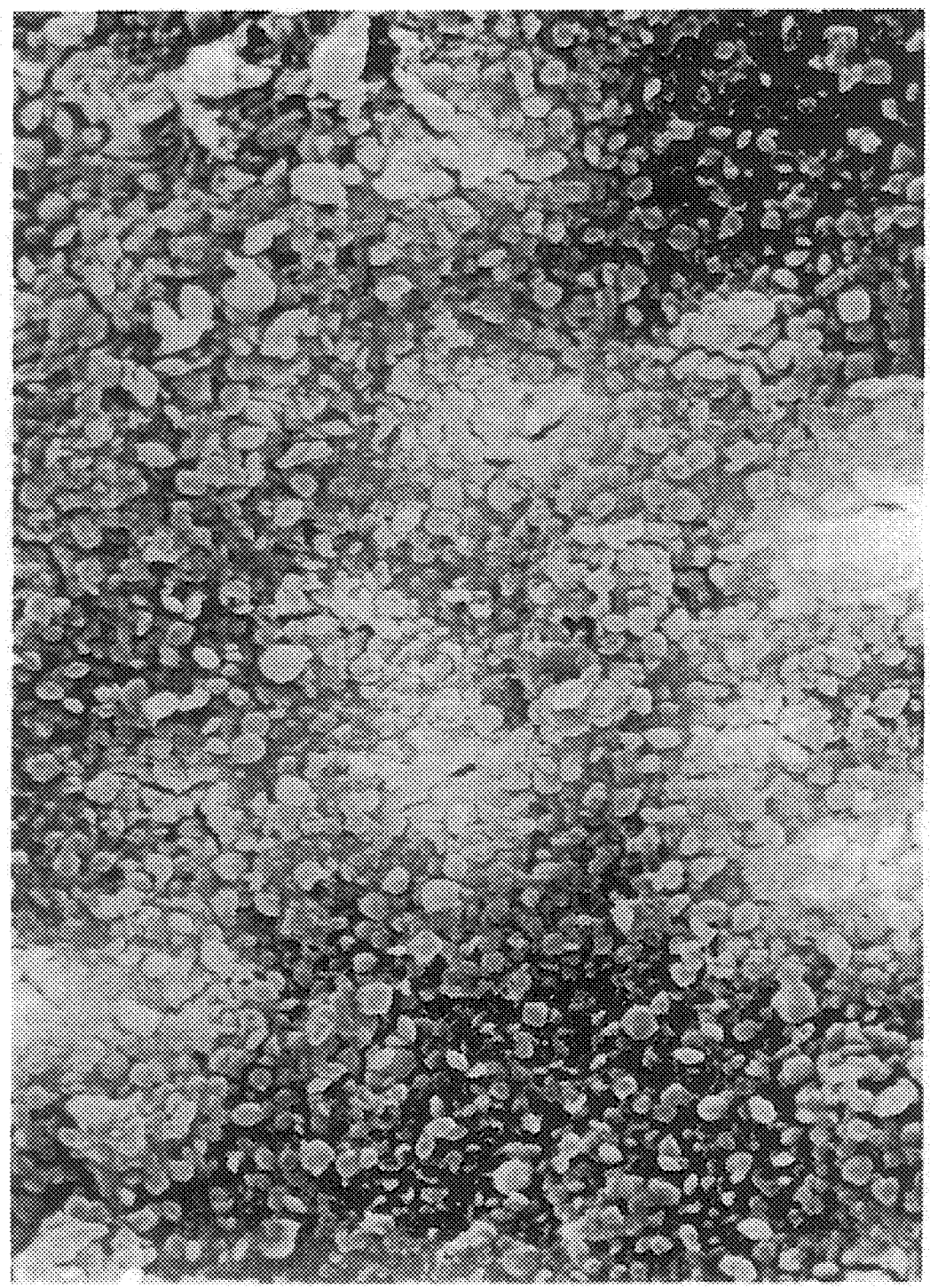
FIG. 2A is a SEM of the surface of mineralized dentin following a 1 minute treatment with 6% dipotassium oxalate followed by water rinsing. Note that the surface is covered with crystals of calcium oxalate which have occluded the tubule orifices but have also covered all surfaces. Attempts to bond resin to such surfaces lead to very low bond strengths (Pashley et al., Am J Dent 6: 116–118, 1993) because the resin bonds to the calcium oxalate crystals which are not firmly attached to the underlying dentin.
Figure 2B:
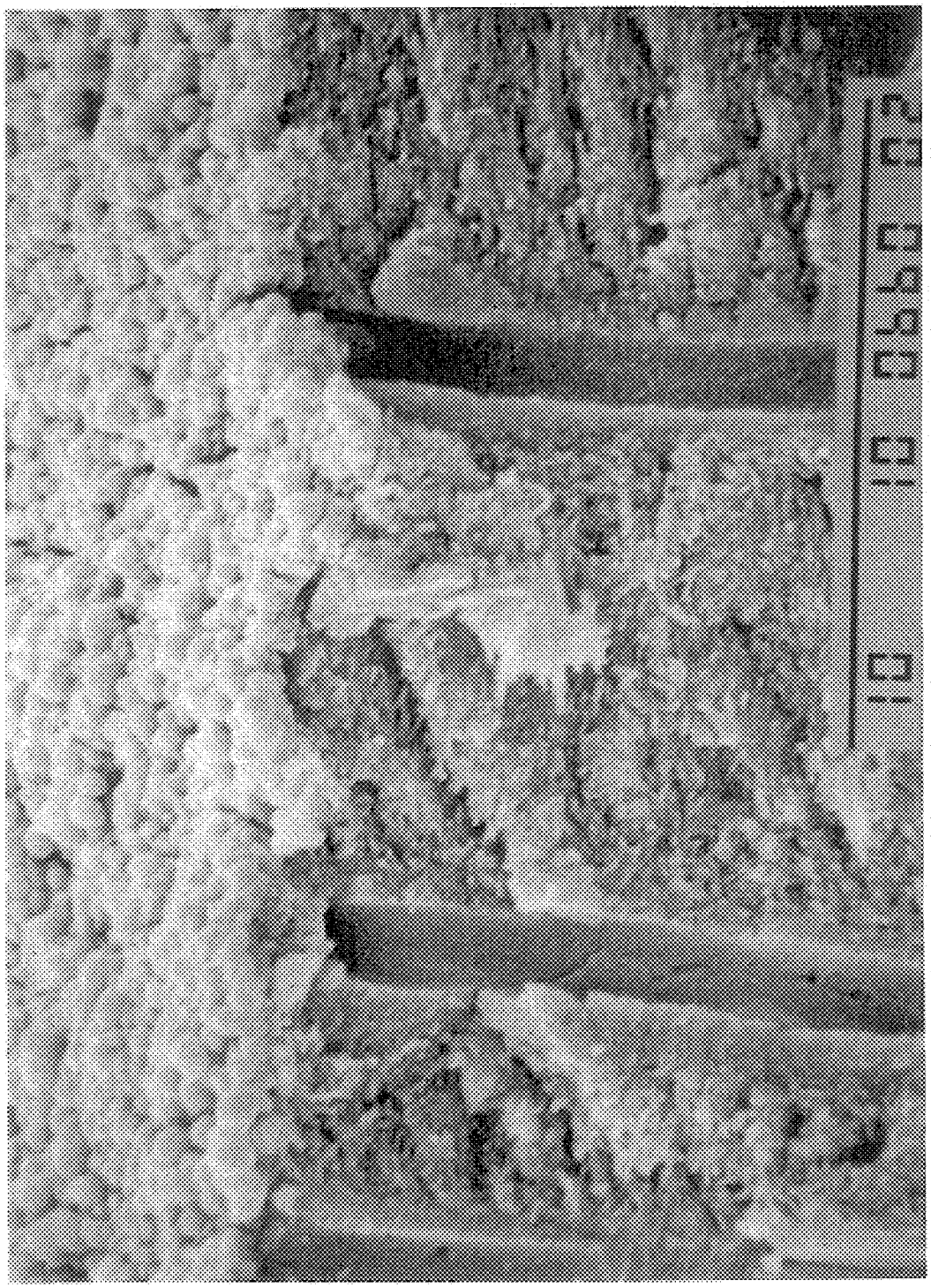
FIG. 2B is a SEM of a fractured edge of a similar specimen. Note that the crystals of calcium oxalate react so rapidly with the mineralized dentin surface that they do not penetrate well into the tubule lumen.
Figure 3A:
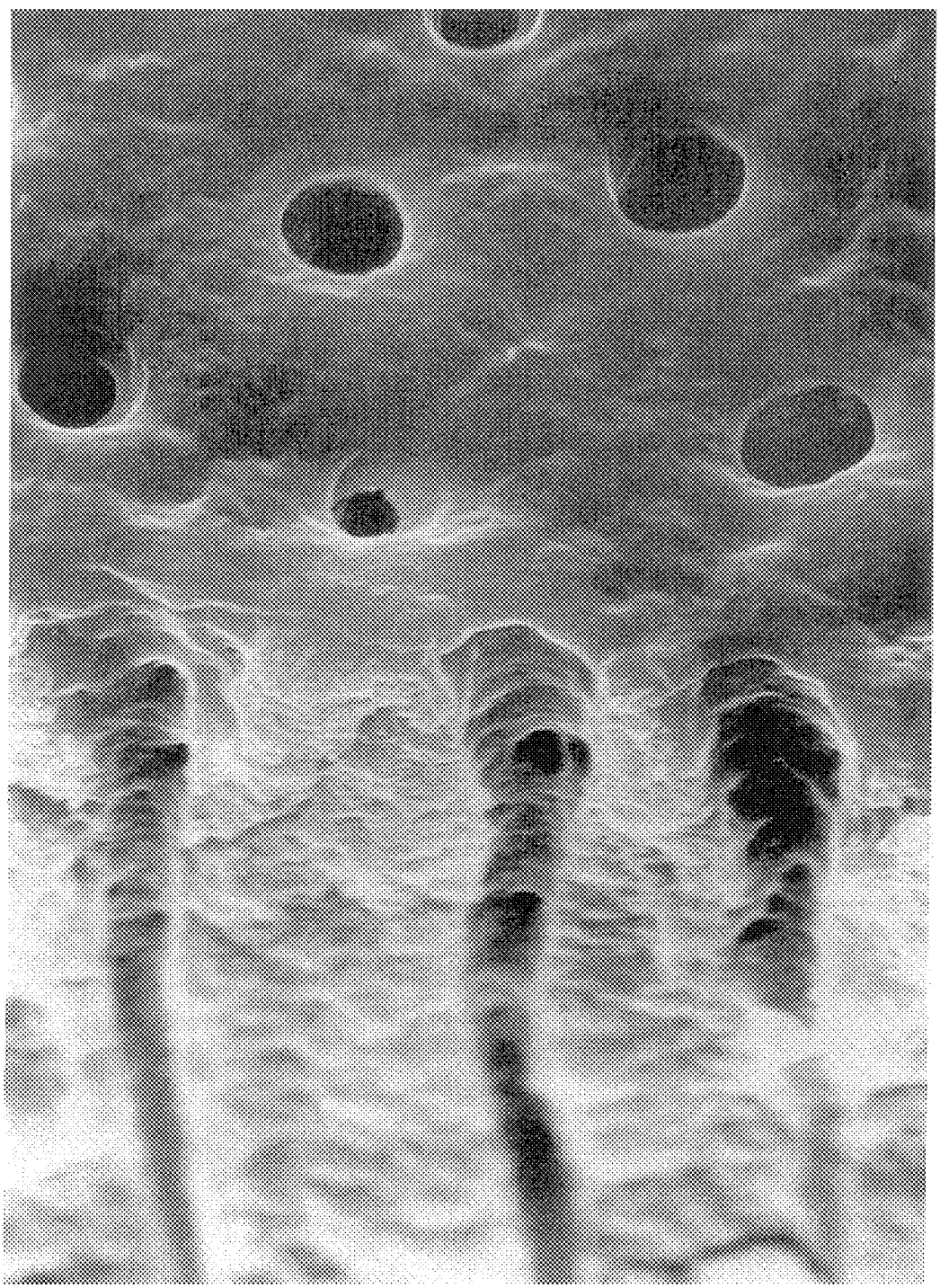
FIG. 3A is a scanning electron micrograph of acid-etched dentin (10% phosphoric acid for 20 seconds) which was then treated with 3% NaCl for 1 min, followed by water rinsing. Note that the topical treatment with NaCl produced no insoluble crystals on the surface. Note also, the smooth, amorphous appearance of the surface and the tubules which are devoid of any intraluminal crystalline material.
Figure 3B:
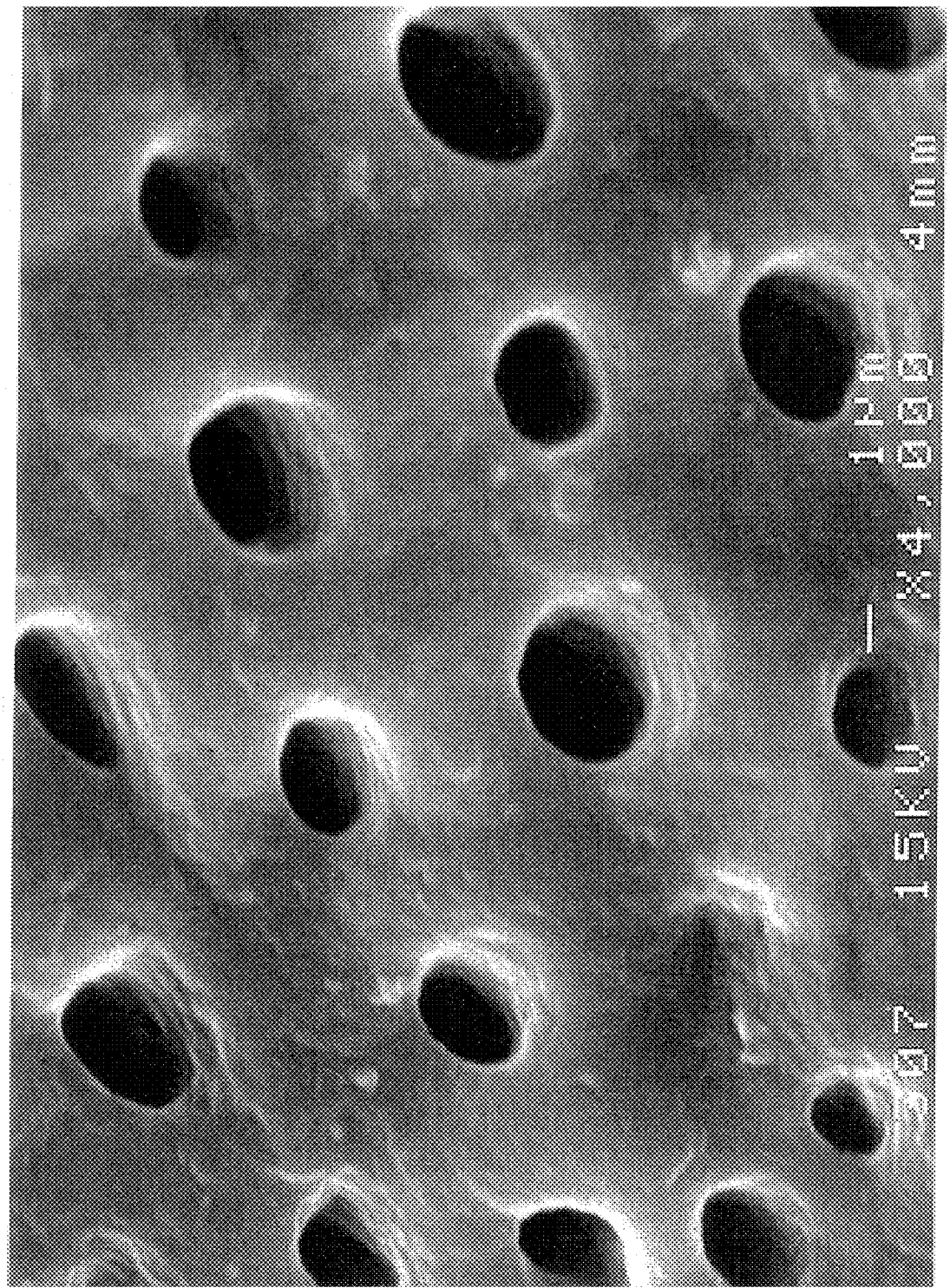
FIG. 3B is a SEM of the surface of acid-etched dentin that was treated with 6% dipotassium oxalate (DKO) gel for 1 min and then rinsed with water. There are no crystals of calcium oxalate on the surface, and the surface looks much like that of the NaCl treated control specimen in FIG. 3A.
Figure 4A:
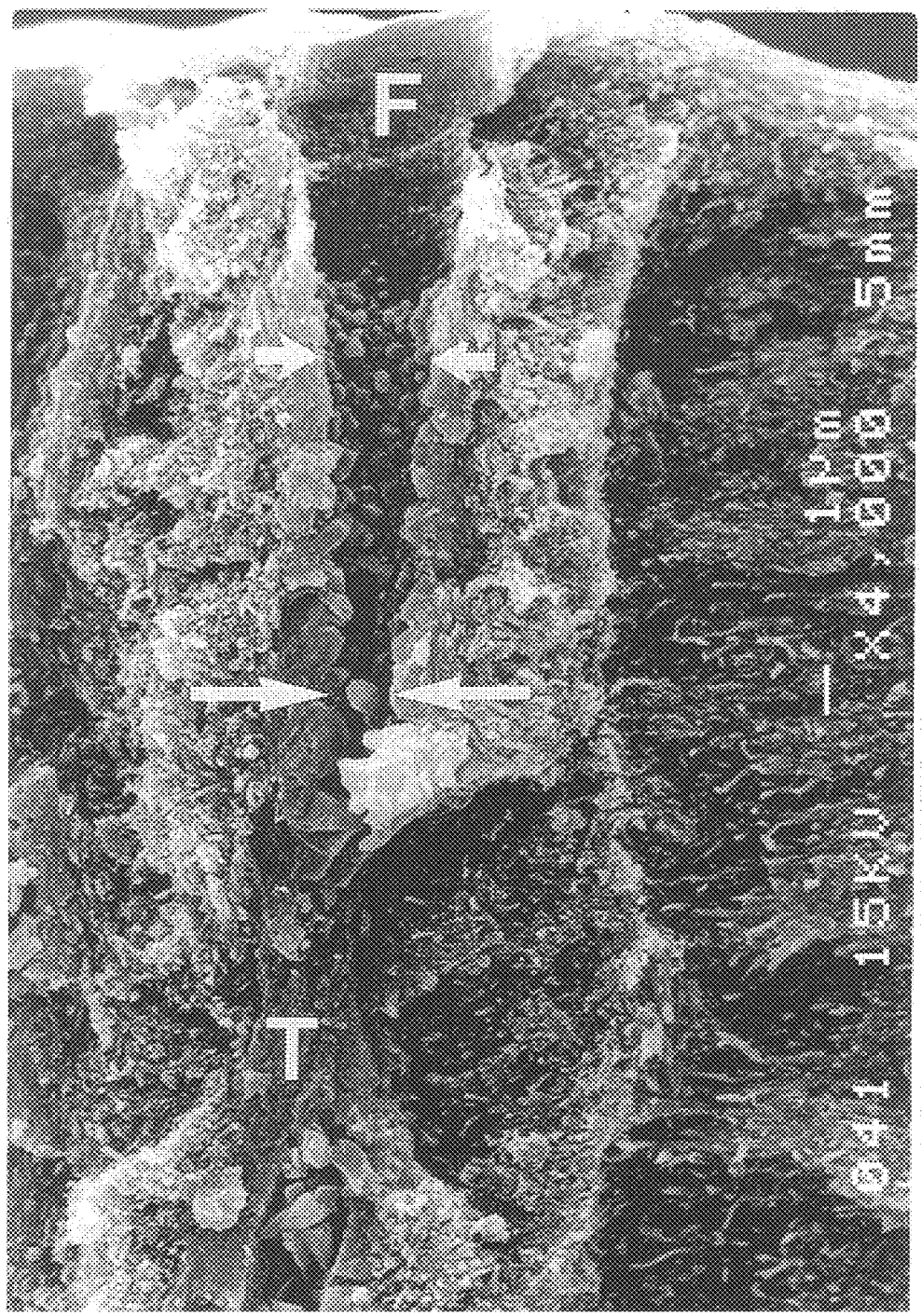
FIG. 4A is a scanning electron micrograph of an acid-etched specimen of dentin that was treated exactly like the specimen shown in FIG. 3B, but was then fractured to permit examination of the tubule contents below the surface. Note the distribution of crystal sizes of calcium oxalate that begin as small crystals in the funneled (F) region of the acid-etched tubules, but grow larger in the deeper regions of the tubules (T). The top 4–5 μm of tubules are free of crystals, which leaves room for resin to occupy the top portion of the tubule when bonding adhesive resins to the surface.
Figure 4B:
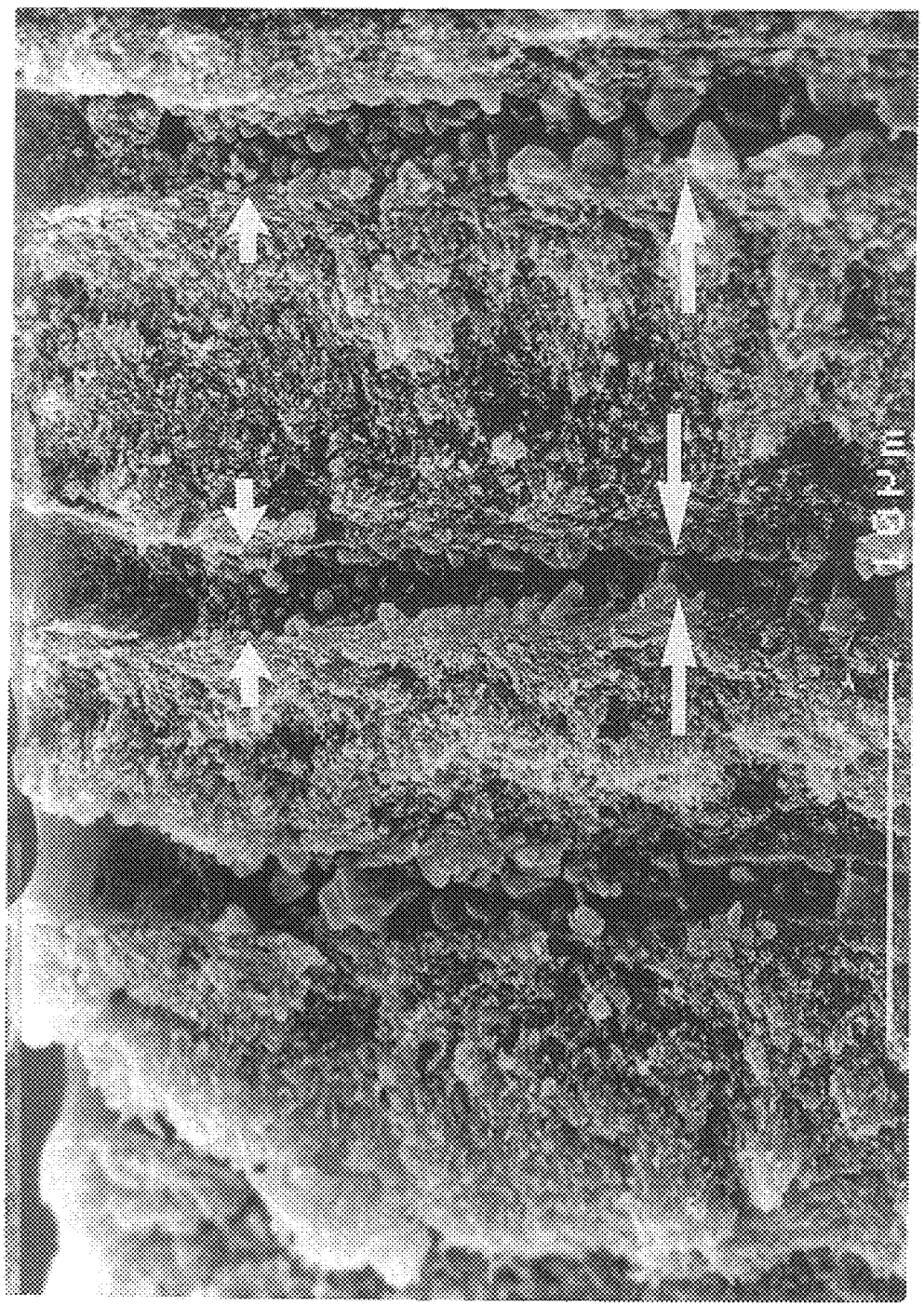
FIG. 4B is a scanning electron micrograph of another fractured specimen of 6% DKO gel-treated acid-etched dentin. The crystals that formed inside the tubules begin as small crystals (location designated by small white arrows), but grew larger in deep regions (designated by large white arrows).

FIG. 1A shows a specimen from Group 1, the mineralized control group. The surface of the dentin is mineralized and the tubules are open, simulating the clinical condition of dentin sensitivity. Another specimen from Group 1 was fractured (FIG. 1B) to demonstrate that the tubules are relatively smooth and empty below the surface. In FIG. 2A, the surface of mineralized dentin was treated with 6% DKO gel for 1 min and then rinsed with water. Scanning electron microscopy (SEM) revealed the entire surface to be covered with small crystals of what has been shown to be calcium oxalate. These crystals not only occluded the tubule orifices but all the dentin surface which intereferes with resin bonding. FIG. 2B shows that the crystals of calcium oxalate are largely limited to the surface when mineralized dentin surfaces are treated with 6% DKO. Few crystals were located within the tubules below the surface. Although this degree of tubule occlusion with calcium oxalate crystals would decrease dentin sensitivity, if these surface crystals were lost by brushing or were slowly solubilized, the tubules would again be open and sensitive. FIG. 3A shows the SEM appearance of a Group 2 specimen that was acid-etched with 10% phosphoric acid for 20 secs, rinsed and then treated with 0.9% NaCl for 1 min, rinsed and then fractured. The SEM appearance of the dentin revealed a smooth amorphous appearance to the surface between open tubules. The fractured surface showed that the tubules had a funnel-shaped appearance due to the preferential removal of peritubular dentin mineral from the top 5–6 um. Indeed, the depth of the funneling indicates the depth of demineralization. The lining of the tubules was devoid of any crystalline material but contained numerous circumferentially-oriented collagen fibrils. FIG. 3B is a surface view of a specimen from Group 3 (acid-etched) that was treated with 6% DKO for 1 min, followed by rinsing with water. The surface is devoid of any crystals of calcium oxalate. However, FIG. 4A shows the subsurface of another oxalate treated specimen in Group 3. Oxalate treatment resulted in no crystal deposition in the top 4 um of the funnel-shaped tubule, but the formation of small calcium oxalate crystals beginning about 4 um below the surface where there was still some residual peritubular dentin material. The crystals became larger in size as the tubule contents were examined further from the dentin surface. This is also shown in FIG. 4B. These intratubular crystals are presumed to be calcium oxalate mono and dihydrate.

Figure 5:
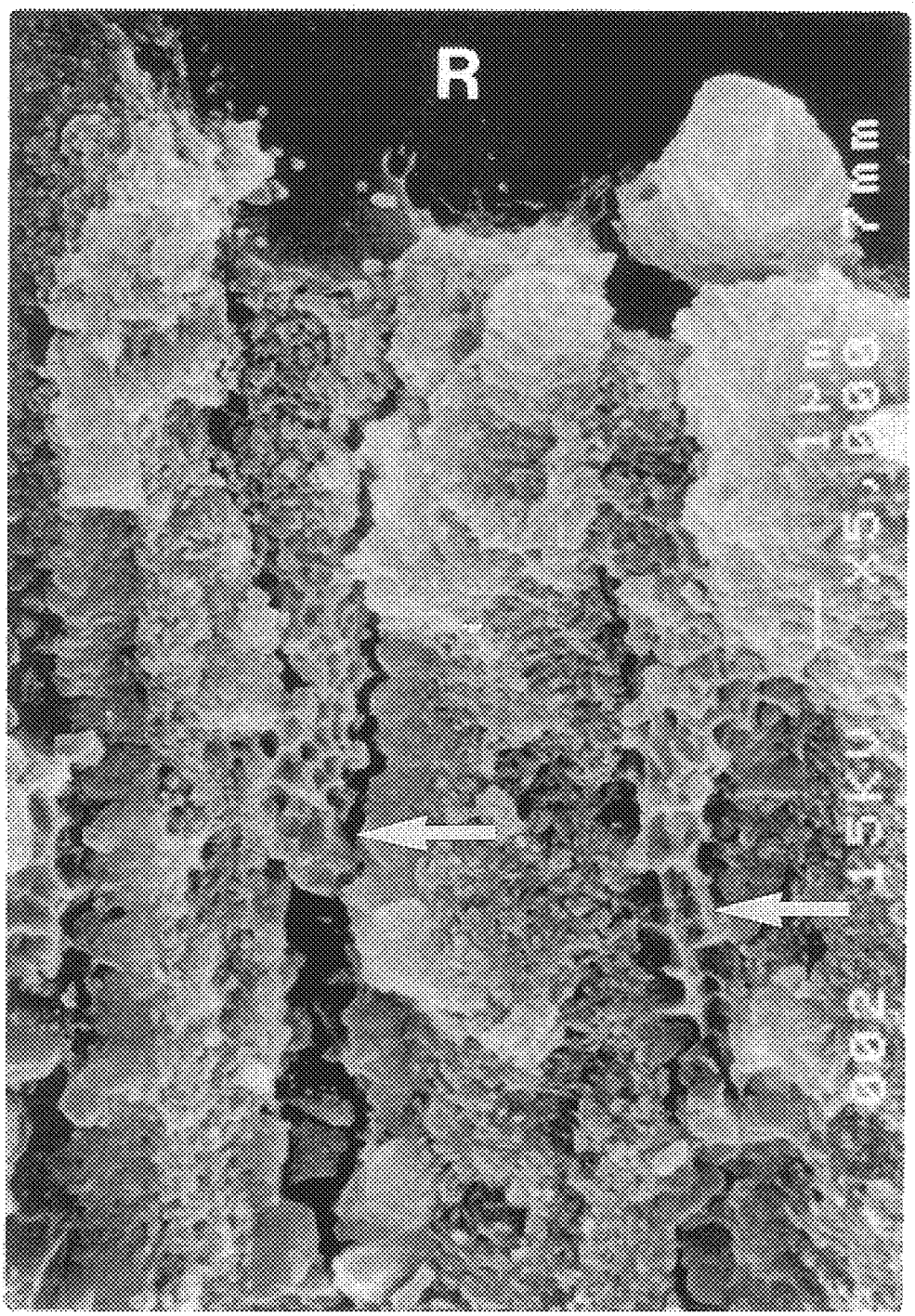
FIG. 5 is a scanning electron micrograph of acid-etched dentin that was treated with 6% DKO gel for 1 min, rinsed and then treated with One-Step bonding resin (R). After light-curing the resin, the specimen was fractured. The top of the resin tag is smooth but the surface of the resin tag extending into the tubule becomes more granular where the resin interacted with small crystals of calcium oxalate. Deeper into the tubule, the surface of the resin tag became more angular where it flowed between larger crystals of calcium oxalate (designated by the large white arrow). The resin did not penetrate much beyond the large crystals because the crystals occluded the tubule lumen. The calcium oxalate crystals were dislodged from the resin tag during specimen fracturing.

FIG. 5 shows an acid-etched specimen of Group 3 that was sequentially treated with the oxalate gel and then the One-Step adhesive bonding system. Resin polymer fills the tubule lumen to a depth of about 10 μm and the surface texture of the deepest half of the resin tags are very rough and angular, just like the texture of the calcium oxalate crystals that are seen in FIGS. 4A and 4B where no resin was applied. When the specimen was fractured for SEM examination, the oxalate crystals adjacent to the resin tags became dislodged and fell out but one can see the angular impressions that they left in the polymer. Since the resin polymer is insoluble in water, these resin-enveloped crystals would have been protected from dissolution and remained in place indefinitely, thereby prolonging their desensitizing effect.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. In the oxalate treatment of dentin sensitivity, the improvement comprising the step of providing an acid, an acidic oxalate, and a bonding agent, from a kit comprising:

a. a first container of an acid treatment composition;
   b. a second container of an acidic oxalate composition; and
   c. a third container of a bonding agent.

2. The kit of claim 1 wherein the acid treatment composition is an acid etchant comprising from about 0.1% by weight to saturation of an acidic ingredient.

3. The kit of claim 1 wherein the acid treatment composition is an acid etchant comprising from about 10% to about 37% by weight $H_3PO_4$.

4. The kit of claim 1 wherein the acidic oxalate has a pH from about 2.0 to about 5.0.

5. The kit of claim 1 wherein the acidic oxalate comprises a residue of one or more alkali metal oxalates, ammonium oxalates, a dihydrogen oxalate, or a mixture thereof.

6. The kit of claim 1 wherein the acidic oxalate comprises a dipotassium oxalate residue.

7. The kit of claim 1 wherein the acidic oxalate comprises from about 0.5% to about 6.0% by weight/volume of a dipotassium oxalate residue.

8. The kit of claim 1 wherein the acid treatment composition is an acid etchant comprising an acidic ingredient having a pKa of less than about 3.0.

9. The kit of claim 1 wherein the bonding agent is hydrophilic.

10. The kit of claim 1 wherein the bonding agent is an adhesive resin, an adhesive cement, a nonadhesive cement, a direct dental restoration, or an indirect dental restoration.

* * * * *